US00PP33323P2

(12) United States Plant Patent
Carruth

(10) Patent No.: US PP33,323 P2
(45) Date of Patent: Aug. 10, 2021

(54) GROUND COVER ROSE PLANT NAMED 'WEKRAHATJACOR'

(50) Latin Name: *Rosa hybrida*
Varietal Denomination: WEKrahatjacor

(71) Applicant: Early Morning LLC, Lawrenceburg, IN (US)

(72) Inventor: Thomas F. Carruth, Altadena, CA (US)

(73) Assignee: Early Morning LLC, Lawrenceburg, IN (US)

( * ) Notice: Subject to any disclaimer, the term of this patent is extended or adjusted under 35 U.S.C. 154(b) by 0 days.

(21) Appl. No.: 17/247,235

(22) Filed: Dec. 4, 2020

(51) Int. Cl.
*A01H 5/02* (2018.01)
*A01H 6/74* (2018.01)

(52) U.S. Cl.
USPC ..... Plt./101
CPC ..... *A01H 6/749* (2018.05)

(58) Field of Classification Search
USPC ..... Plt./101
CPC ..... A01H 6/749; A01H 5/02
See application file for complete search history.

(56) References Cited

U.S. PATENT DOCUMENTS

PP19,646 P2 1/2009 Ilsink
PP28,655 P3 11/2017 Carruth

OTHER PUBLICATIONS

"JAChaneflocba Rose", https://www.helpmefind.com/rose/.1.php?1=2.84204.1, 1 page, accessed Feb. 24, 2021.

*Primary Examiner* — Keith O. Robinson
(74) *Attorney, Agent, or Firm* — McKee, Voorhees & Sease, PLC

(57) ABSTRACT

A new variety of Ground Cover rose suitable for garden decoration, having flowers of red with large yellow eye coloration.

1 Drawing Sheet

Classification: The present invention relates to a new *Rosa hybrida* plant.

Variety denomination: The new plant has the varietal denomination 'WEKrahatjacor'.

BACKGROUND OF THE INVENTION

This invention relates to a new and distinct variety of Ground Cover Rose. It has as its seed parent the variety known as 'WEKsurdicla' (U.S. Plant Pat. No. 28,655) and as its pollen parent the variety known as 'JAChaneflocba' (not patented).

SUMMARY OF THE INVENTION

Among the features which distinguish the new variety from other presently available and commercial rose cultivars known to the inventor are the following combinations of characteristics: its low trailing spreading growing habit, its unusual for the class brightly colored flowers of red with large yellow eye and its vigorous growth. The plant has a trailing spreading growing habit, suitable for outdoor garden decoration.

Asexual reproduction of the new variety by budding as performed in Kern County, Calif., shows that the foregoing and other distinguishing characteristics come true to form and are established and transmitted through succeeding asexual propagations. 'WEKrahatjacor' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, 'WEKsurdicla' by the following combination of characteristics: whereas 'WEKrahatjacor' bears single flowers (about 5 to 7 petals) of red with large yellow eye coloration, 'WEKsurdicla' bears double flowers of yellow edged pink coloration with significantly heavier petalage (about 20 to 30 petals). The new variety bears small flowers (about 4.8 to about 5.0 cm. in diameter), whereas the seed parent bears significantly larger flowers (about 5.5 to about 7.5 cm. in diameter).

The new variety may be distinguished from its pollen parent, 'JAChaneflocba' by the following combination of characteristics: whereas 'WEKrahatjacor' bears single flowers (about 5 to 7 petals) of red with large yellow eye coloration, 'JAChaneflocba' bears semi-double flowers of orange with bright yellow eye coloration with significantly heavier petalage (about 8 to 12 petals). The new variety has a trailing and spreading low growing habit (about 21 to about 28 cm. in height), whereas the pollen parent has spreading and bushy significantly taller growing habit (about 41 to about 52 cm. in height).

COMPARISON WITH THE CLOSEST COMMERCIALLY AVAILABLE CULTIVAR

The new variety may be distinguished from its closest commercially available cultivar, 'INTERhappy' (U.S. Plant Pat. No. 19,646) by the following combination of characteristics: whereas 'WEKrahatjacor' bears small flowers (about 4.8 to about 5.0 cm. in diameter) of red with large yellow eye coloration, 'INTERhappy' bears smaller flowers (about 4.0 cm. in diameter) of yellow-orange coloration. The new variety has a trailing and spreading low growing habit (about 21 to about 28 cm. in height), whereas the closest commercially available cultivar has a vigorous sprawling significantly taller growing habit (about 60 cm. in height).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Wasco, Calif. in the month of November. Throughout this specification, color references and/or values are based upon The Colour Chart of The Royal Horticultural Society (2001) except where common terms of color definition are employed.

DESCRIPTION OF THE NEW VARIETY

The following description is of 3 to 4 year-old rose plants of the new variety grown outdoors in Wasco, Calif. in the month of November. Phenotypic expression may vary with environmental, cultural and climatic conditions, as well as differences in conditions of light and soil.

FLOWER

The new variety usually bears its flowers in clusters of three to five per stem. Flowers are borne in rounded to pyramidal clusters on strong medium length stems (about 30 to about 40 cm.). The cluster ranges from about 3.0 to about 5.0 cm. in diameter. Outdoors, the plant blooms abundantly and nearly continuously during the growing season. The flowers have a slight tea fragrance.

BUD

The peduncle is about 2.0 to about 2.3 cm. in length, of slender caliper (about 0.2 cm. in diameter), and usually stiff. It is almost entirely smooth, with many very fine hairs. Peduncle color is near 148C often heavily suffused, especially on the side exposed to the sun, with between 178B and 178C.

Before the calyx breaks, the bud is about 0.8 to about 0.9 cm. in diameter at the widest point, about 1.5 to about 1.6 cm. in length, and pointed to ovoid in shape with a conspicuous neck. The surface of the bud bears between 5 to 7 foliaceous appendages with a few stipitate glands, usually with slender entire foliaceous parts extending beyond the tip of the bud about ¼ or more of its length. Bud color is near 137D and sometimes suffused, especially on the side exposed to the sun, with near 178A.

The sepals are 5 per flower, about 1.9 to about 2.0 cm. in length and about 0.6 to about 0.7 cm. in width at the widest point. The outer surface color of the sepal is near 137D and often heavily suffused, especially on the side exposed to the sun, with near 178A. The outer surface of the sepal is smooth and bears between 0 to 3 small foliaceous appendages with a few stipitate glands. The inner surface color of the sepal is near 138C. After the sepals open, the inner surface color is sometimes lightly suffused, especially on the area exposed to the sun, with between 185C to 185D. The inner surface of the sepal is covered with fine wooly tomentum; sepal margins are entire and lined with few stipitate glands. The sepals are permanent, and usually spear-shaped to recurved in shape with acute apices.

The receptacle of the flower is of somewhat short length (about 0.7 to about 0.8 cm.) and moderately thin in caliper (about 0.6 to about 0.7 cm. in diameter). The receptacle is somewhat ovoid to globular in form. Its surface is very smooth with thick fleshy walls. The receptacle color is near 138B and is often suffused on the area exposed to the sun with 185A.

As the petals open (after the calyx breaks), the bud is about 1.2 to about 1.3 cm. in diameter at the widest point, about 2.0 to about 2.1 cm. in length, and pointed to ovoid in form. The color of the under surfaces of the newly opened petals is between 46B and 47D. At the point where the petal attaches, there is a small zone of near 12A. The color of the upper surfaces of the newly opened petals is near 146B on the upper two thirds of the petal and the lower one third is 12C. At the point where the petal attaches, there is a small zone of 12A.

BLOOM

When fully open, the bloom ranges from about 4.8 to about 5.0 cm. in diameter. Petalage is single with about 5 to 7 petals and about 0 to 1 petaloids irregularly arranged. When partially open, the bloom form is cupped with petal edges somewhat reflexed outward. When fully open, the bloom form is flat to very slightly cupped, and the petals are flat to slightly undulated with petal edges moderately reflexed outward to somewhat rolled.

PETALS

The substance of the petals is moderately heavy and of medium thickness, with upper surfaces slightly shiny to satiny and under surfaces matte. The petals are about 1.9 to about 2.1 cm. in length and about 2.1 to about 2.3 cm. in width at the widest point. Petal margins are mostly entire.

The petals are orbicular to obovate in shape with rounded apices to cuspidate.

Petaloids are about 1.2 to about 1.5 cm. in length and about 0.5 to about 0.7 cm. in width at the widest point. Petaloids are shaped narrowly spatulate with rounded apices.

NEWLY OPENED FLOWER

The under surface color of the petals is between 46B and 47D. At the point where the petal attaches, there is very small zone of near 12A. The upper surface color of the petals is near 46B on the upper two thirds of the petal changing to 12C on the lower third. At the point where the petal attaches, there is a very small zone of 12A.

The under and upper surface colors of the petaloids are similar in coloration to the upper and under surfaces of the petals.

The general tonality of the newly opened flower is near 46B on the upper two thirds of the flower changing to 12C on the lower third.

THREE-DAY-OLD FLOWER

The under surface color of the petals is between 46A and 46D. At the point where the petal attaches, there is a small zone of near 13D. The upper surface color of the petals is between 46A and 46D. At the point where the petal attaches, there is a small zone of near 13D.

The under and upper surface colors of the few petaloids are similar in coloration to the upper and under surfaces of the petals.

The general tonality of the three-day-old flower is between 46A to 46D.

On the spent bloom, the petals usually drop off cleanly.

In November in Wasco, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 75) and are arranged regularly about the pistils; a few are mixed with a rare petaloid. The filaments are of medium to long length (about 0.6 to about 0.7 cm.) most with anthers. Filaments are near 14B in color. The anthers are of medium size for the class and all open approximately at the same time. Anther color when immature is near 22A on the external part and near 22C on the internal part. Anther color at maturity is near N167A on the external part and near N167D on the internal part. Pollen is moderately abundant and near 177B in color.

FEMALE REPRODUCTIVE ORGANS

Pistils vary in number (average about 25). The styles are somewhat uneven, short in length (about 0.2 to about 0.3 cm.), average in caliper, and bunched. Stigma color is between 157B and 157C. Style color is near 146A. Ovaries are generally enclosed in the calyx. The ovaries are of medium size and between 157B and 157C in color.

Hips are somewhat short to average in length (about 1.2 to about 1.3 cm.), globular in form, and near 146A when green mature and in N34C color when fully ripe. The hip surface is very smooth with thick fleshy walls.

The seeds are irregularly rounded, smooth in texture, approximately 4 to about 5 per hip, about 0.4 to about 0.5 cm. in diameter at the widest point and near 165C in color.

FOLIAGE

The compound leaves are usually comprised of three to five leaflets and are borne abundantly. The five-leaflet leaves are about 8.0 to about 8.5 cm. in length and about 5.5 to about 5.8 cm. in width at the widest point, leathery in texture on both sides, and somewhat glossy in finish on the upper side and matte in finish on the under-side. The leaves have a pinnate venation pattern. The terminal leaflets are about 3.6 to about 3.8 cm. in length and about 2.1 to about 2.3 cm. in width at the widest point, shaped oval with mucronate apices and oblique bases. Their margins are simply serrate.

The upper surface color of the mature leaf is between 139A and 138A. The under-surface color of the mature leaf is near 138A. The under and upper colors of the leaf veins on the mature leaf are similar in coloration to the upper and under surfaces colors of the mature leaf. The upper surface color of the young leaf is between 183A and 183B. The under-surface color of the young leaf is near 183B. The under and upper colors of the leaf veins on the young leaf are similar in coloration to the upper and under surfaces colors of the young leaf.

The rachis is about 4.3 to about 4.7 cm. in length, about 0.1 cm in width at the widest point, and moderately rough. The upper side is shallowly grooved with few hairs on the edges of the grooves. The under-side of the rachis is moderately rough with few stipitate glands and small prickles. The rachis color is near 138A on the under-side and near 139A on the upper side.

The stipules are about 0.6 about 1.0 cm. in length and narrow (about 0.3 to about 0.4 cm.) with medium length straight points that usually turn out at an angle of more than 45 degrees and sometimes recurve toward the stem. The under and upper surface color of the stipule is between 139A and 138A. The upper and under surfaces of the stipules are smooth in texture.

The petiole is light in caliper and smooth. The upper side is shallowly grooved with few hairs on the edges of the grooves. The under-side is smooth with few hairs. The petiole is about 0.1 cm. in length and about 0.1 cm in width at the widest point. The petiole color is near 138A on the under-side and near 139A on the upper side.

The plant displays an above average degree of resistance to powdery mildew (*Sphaerotheca pannosa*), downy mildew (*Peronospora sparsa*) and rust (*Phragmidium* sp.) as compared to other commercial varieties grown under comparable conditions in Wasco, Calif. The plant's winter hardiness and drought/heat tolerance are yet to be determined.

GROWTH

The plant has a trailing and spreading low growing habit (about 21 to about 28 cm. in height and about 72 to about 92 cm. spread at the widest point), with full branching. It displays vigorous growth and the canes are of light to medium caliper for the class (about 0.4 to about 0.8 cm. in diameter at the widest point).

The color of the major stems is near 138B. The major stems are rough in texture and they bear several large prickles that are about 0.5 to about 0.7 cm. in length. The large prickles are almost straight and angled moderately downward with a medium length narrow base; prickle color is between 200B and 200C. The major stem bears few small prickles of similar shape and coloration.

The color of the branches is between 138B and 138C. The branches are rough in texture and they bear several large prickles which are of similar size and shape to the large prickles on the major stems; prickle color is between 179A and 179B. The branches bear few small prickles of similar shape and coloration.

The color of the new shoots is between 178A and 178B. The new shoots are rough in texture and they bear several large prickles which are of similar size and shape to the large prickles on the major stems; prickle color is near 178A. The shoots bear few small prickles of similar shape and coloration.

I claim:

1. A new and distinct Ground Cover rose plant of the variety substantially as described and illustrated herein.

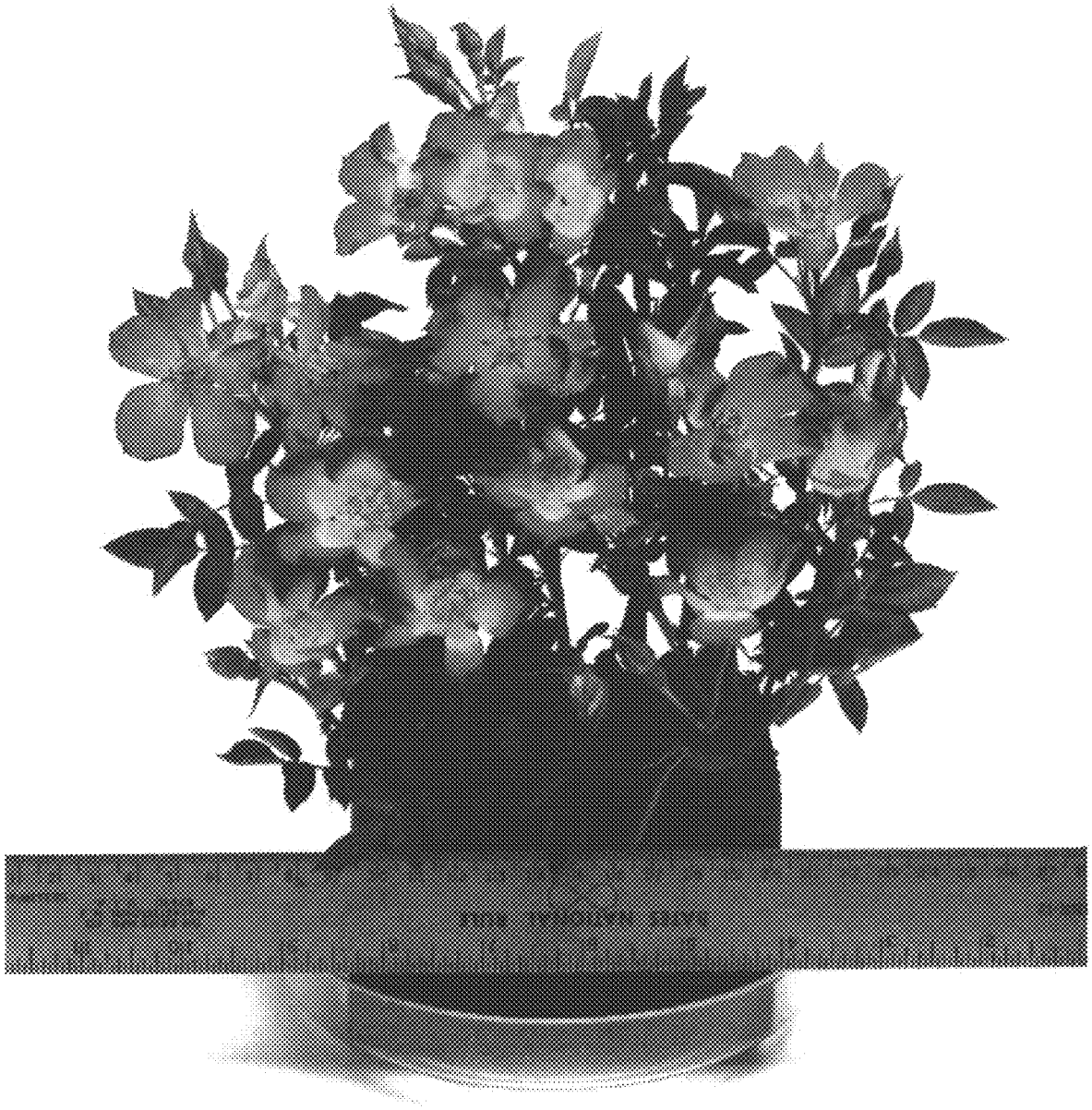

* * * * *